United States Patent [19]
Holfert

[11] Patent Number: 5,089,014
[45] Date of Patent: Feb. 18, 1992

[54] TUBULAR INTERCONNECT DEVICE FOR USE WITHIN THE CIRCULATORY SYSTEM

[76] Inventor: John W. Holfert, 109 W. 2700 So., Bountiful, Utah 84010

[21] Appl. No.: 51,578

[22] Filed: May 18, 1987

[51] Int. Cl.$^5$ .............................................. A61F 1/24
[52] U.S. Cl. ...................................................... 623/2
[58] Field of Search ................. 623/2, 3; 285/12, 354; 128/1 R, 334 R, 334 C

[56] References Cited

U.S. PATENT DOCUMENTS

| | | | |
|---|---|---|---|
| 98,774 | 1/1870 | Fitzgerald | 285/354 |
| 710,768 | 10/1902 | Ford | 285/354 |
| 714,724 | 12/1902 | Marsh | 285/354 |
| 764,881 | 7/1904 | Colin | 285/354 |
| 2,897,835 | 8/1959 | Philippe | 623/2 |
| 3,625,745 | 12/1971 | Wright | 623/2 |
| 4,118,806 | 10/1978 | Porier et al. | 623/3 |
| 4,376,312 | 5/1983 | Robinson et al. | 623/3 |
| 4,534,761 | 8/1985 | Raible | 623/12 |
| 4,588,404 | 5/1986 | Lapeyre | 623/3 |

FOREIGN PATENT DOCUMENTS 0092762 5/1985 Japan ......................................... 623/3

Primary Examiner—David J. Isabella

[57] ABSTRACT

A tubular interconnected device for coupling within the circulatory system of a living being. The device includes first and second connective members formed of rigid materials of high tolerance construction. The connective members each have an internal sealing edge with mating faces for developing sealing contact when interlocked. A sleeve is attached to one of the connective members and operates with respect to the second connective member to draw the two into an aligned, locked configuration, with force imposed at the sealed junction of the mating faces. Distal edges at the extremities of each connective member are permanently sealed to open ends of the circulatory system to which the interconnect device is coupled. Specific structure is disclosed for use in connectioin with an artificial heart implant.

13 Claims, 3 Drawing Sheets

TUBULAR INTERCONNECT DEVICE FOR USE WITHIN THE CIRCULATORY SYSTEM

BACKGROUND OF THE INVENTION

1. Field of Invention

This invention pertains to a fabricated interconnect device for coupling between open ends of the vascular or arterial flow line within a human circulatory system. More particularly, the present invention relates to an interconnect device for enabling implantation of a total artificial heart, ventricular assist device or for similar applications wherein the arterial or vascular network of the body must be repaired or modified to redirect blood flow.

2. Prior Art

Modern medicine has developed many procedures and devices relating to treatment and care of patients with disorders of the circulatory system. Frequently, treatment procedures require the physician to interrupt the natural vascular or arterial network by inserting replacement valves, shunting devices and other prosthetics within the flow line of the circulatory system. Representative examples of such treatment procedures include the use of aortic and arterial-venus shunting, bypass and cardiac assist devices, and more recently, the total artificial heart. It is perhaps in this last area of heart implantation that the acute risks of modifying or interferring with blood flow in the circulatory system are most evident. Without exception to date, each patient having a permanent total artificial heart implant has succumbed to the affects of thrombogenesis and thromboembolism. These difficulties have also been the focus of research in an effort to develop a successful clinical program utilizing the total artificial heart as a bridge to later cardiac transplantation.

During the time that a patient's life is dependent upon the artificial heart, he is subject to an extreme high risk of thrombogenesis or thrombus formation. These emboli break free from their point of origin and frequently travel to the brain resulting in thromboembolism and the attendant effects of stroke. In view of this high risk, clinical practice attempts to minimize support time on the artificial heart to the shortest possible period because of the potential for stroke and attendant brain damage. Even use of the artificial heart in experimental animals has revealed that thrombus formation is a common observation for current devices even for short implant periods.

Successful implacement of the artificial heart requires quick attachment of the device to the left and right atria, aorta and pulmonary arteries. The attachment procedures are very difficult because of the restricted space and visual impairment resulting from excessive flow of blood. Consequently, the dominant devices for attaching the arteries to the artificial heart have been quick connect valves such as are illustrated in FIG. 1. This system relies on a polyurethane graft or cuff for developing a total seal on a rigid valve-holding ring 11 which includes a lip 12 adapting the cuff 10 for snap-in-place attachment. The cuff is modified with an attachment flange 13 which includes a shoulder designed to snap in place over the lip 12 to secure the cuff 10 and valve-holding ring together. The holding ring 11 includes a movable valve element 14 which is secured to a valve support ring 15. The valve support ring 15 is sandwiched between a retaining shoulder 16 of the holding ring 11 and an high durometer plastic holding ring 17 which includes a retaining shoulder 18 for securing the valve support ring 15 in place. The artificial heart body or BIOMER ™ (a polyethlene polyurethane assigned to Ethicon, New Brunswick NJ) housing 19 is adhesively coupled to the ISOPLAST ™ (a polyethylene polyurethane assigned to Dow Chemical Co., Inc.) valve holding ring 17.

Prior to inserting the high durometer plastic valve holding ring 17 into its companion valve-holding ring 11, the metallic support ring 15 is inserted within the plastic ring 17 as shown in FIG. 1. This combination is then inserted or screwed into the receiving channel 20 formed in the valve-holding ring 11. Sealing contact at shoulder 16 by the adjacent side edge of the valve support ring 15 is based on contact arising from the pressure applied when inserting this plastic ring and attached support ring in interlocking position.

A major cause of thrombogenesis within this valve arrangement are small gaps which occur between the metallic support ring 15 and shoulder face 16. Similar thrombus formation regularly occurs at the opposite contacting side of the metallic support ring 15 on shoulder 18. In addition, thrombogenesis is also common at the quick connect junction 21 between the arterial cuff 10 and rigid valve housing 11. Gaps in this region arise because of fatigue which reduces tension at the quick connect site, as well as imperfections in construction of the BIOMER-coated cuff 10 and nonuniform forces applied by the surrounding organs and tissue of the body. Those skilled in the art of solution casting for soft polyurethanes are well aware of the difficulty of structuring a fabricated body with uniform strength and elasticity along all directions. The resultant occurrence of shrinkage or imbalance of thickness due to viscosity differences contributes to gap formation when coupled to the rigid plastic valve housing 11. It is also well known that the polyurethane body has a tendency to creep or shift position which can lead to unexpected stresses around the quick-connect location. In addition, nonuniform response to temperature can result in gap formation at the quick-connect location.

The quick-connect device illustrated in FIG. 1 also presents difficulties for the surgeon during implantation. Because of the presence of fluids and impaired observation due to blood flow, the surgeon must rely upon his sense of feel to detect proper positioning of the cuff 10 at the quick couple location. If the cuff is inserted too far or if the cuff fails to be properly set in place, gap formation is likely and thrombosis will be the natural result. If the physician snaps the cuff in place in an incorrect orientation, a tool is required to release the quick connect configuration. Use of this tool may result in local fatigue where the soft plastic is pried apart from the shoulder 12. This quick-connect configuration also limits the surgeon's ability to freely rotate the valve housing so that optimum positioning can take place for the artificial heart. The combination of these problems creates a complex challenge for the surgeon, who is already severely limited in time and working space.

OBJECTS AND SUMMARY OF THE INVENTION

It is therefore an object of the present invention to provide a tubular interconnect device which prevents the formation of gaps or incorrect coupling conditions which have heretofore resulted in thrombogenesis within the interconnector system.

It is a further object of this invention to provide such a tubular connect device which can more easily be implaced by a physician, conveniently rotated to proper orientation and quickly aligned and locked in a sealed flow line structurally adapted to avoid gap formation or other defect development which typically contributes to thrombogenesis.

It is a further object of the present invention to provide a tubular interconnect device useful for implantation of a total artificial heart.

It is a still further object of this invention to provide such an interconnect device for use as a shunt to provide unobstructed blood flow without thrombus formation.

Yet a further object of this invention is to provide an interconnect device which is readily adaptable for attachment of a variety of commercial valves which are used in medical procedures within the circulatory system.

These and other objects are realized in a tubular interconnect device for coupling between open ends of a flow line within the circulatory system. The device includes first and second rigid connective members of annular configuration which include biocompatible interior surfaces. Each connective member has a distal edge adapted for attachment to the open ends of the flow line, and an internal sealing edge configured with a mating face for developing sealed contact therebetween in response to forces applied along the connective members and toward a medial sealed juncture. An exterior coupling ring or other sleeve means for interlocking the first and second connective members is also provided. The sleeve aligns and locks the respective connective members together in a coaxial, abutting configuration at the internal sealing edges. It also develops opposing connective forces along each connective member and toward the medial sealed juncture to maintain the absence of gaps or other defects which give rise to thrombogenesis. A valve insert may be provided within the interconnect device to control direction of blood flow therethrough. The subject device has demonstrated surprising effectiveness in reducing thrombus formation and thromboembolism for even the most difficult circumstances of artificial heart implantation.

Other objects and features of the present invention will become apparent to those skilled in the art in view of the following detailed description, taken in combination with the accompanying drawings.

DETAILED DESCRIPTION OF THE INVENTION

Figure 2:
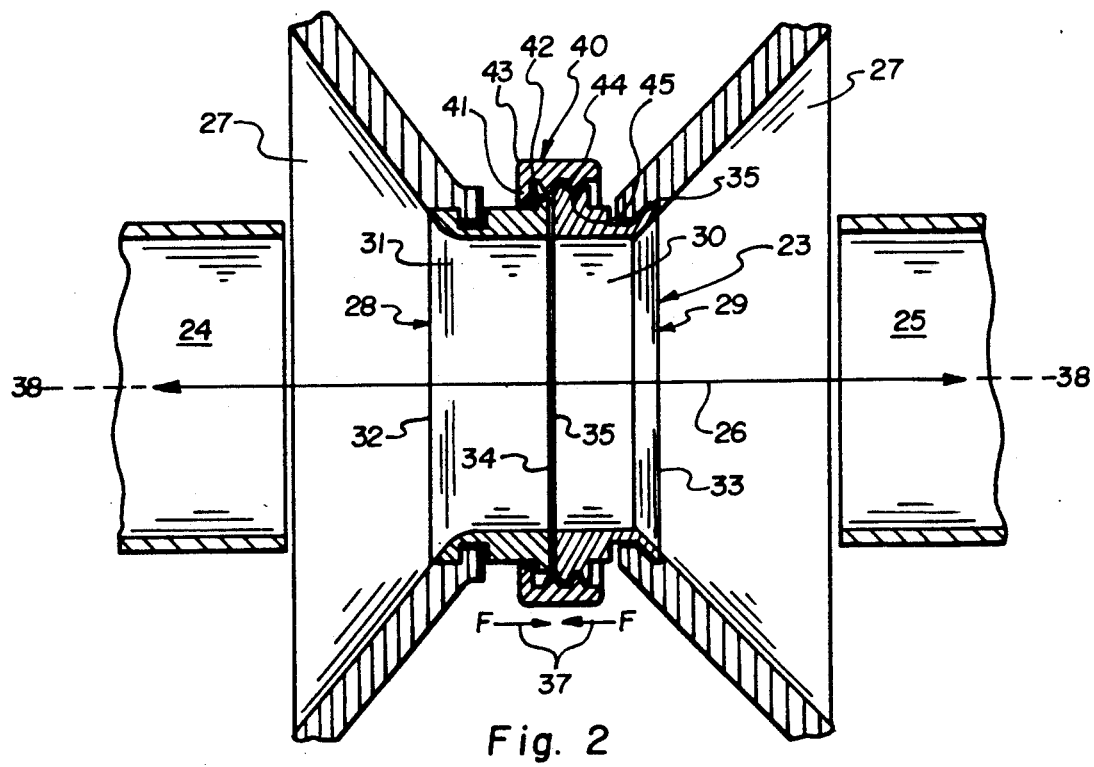
FIG. 2 illustrates a cross section of the present invention forming an interconnecting tube between two open ends of a circulatory system.

FIG. 2 generally illustrates a tubular interconnect device 23 which may be utilized for coupling between open ends 24 and 25 of a flow line 26 which continues into the circulatory system of a living being. Open ends 24 and 25 might be severed portions of the arterial or vascular system, or could be other natural tissue to which a fabricated interconnecting device is attached. Cuff or graft material 27 is represented and would be sutured or otherwise fixed to the open ends 24 and 25 to interconnect the flow line. It will be understood by those skilled in the art that the graphic representation of FIG. 2 is not intended to be a representation of particular tissue or graft material. Likewise, the shape and configuration will of necessity be prepared for a specific location or use. Accordingly, elements 24, 25 and 27 are merely representations of elements and not of particular structure.

The tubular interconnect device 23 comprises first 28 and second 29 rigid connective members. These are so named because they cooperate to connect the respective open ends 24 and 25 to a single flow line, sealing the line against leakage and also providing appropriate interior surface structure for blood compatibility with reduced or minimal thrombogenesis. Each connective member 28 and 29 has an annular configuration which includes a smooth interior surface 30 and 31 of biocompatible material. These interior surfaces extend from opposing distal edges 32 and 33 at the extremities of the device to an abutting junction of internal sealing edges 34 and 35 which are medially positioned along the length of the device.

Reference to medial position is intended to generally describe the location of these sealing edges as being between the distal edges 32 and 33. It will be understood, therefore, that the illustration of sealing edges 34 and 35 approximately half way between the distal edges 32 and 33 could just as well be modified to show the sealing edges displaced to one side or the other, more proximate to the distal edges.

Each distal edge includes means for permanent attachment to the cuff or graft material 27. In FIG. 2, the graft material includes a fabricated receiving channel 35 which mates with the distal edge to secure full sealing contact. Such contact is maintained by adhesive material which permanently joins the interconnect device 23 to the flow line. In this sense, the means for permanent sealed attachment of the distal edges to the flow line includes the graft 27, adhesive and compatible mating structure which develop an appropriate sealed distal juncture which conforms to distal edges 28 and 29.

This juncture is typically coated with BIOMER, TM or other surface treatment to develop a smooth, continuous and biocompatible interior surface extending from each end of the flow line to the interior surface of the respective first and second connective members. Based on this treated surface, no leakage or thrombus formation would be expected to occur at the sealed distal juncture.

The internal sealing edges 34 and 35 are configured with mating faces shown in juxtaposed position in FIG. 2. These faces are carefully machined or otherwise prepared to establish total sealing contact therebetween and to form a medial sealed juncture when forcefully brought together. This is made possible, in part, because of the use of rigid materials on each side of the juncture.

The respective sealing edges 34 and 35 are further prepared to provide a nonobstructive medial interior surface at the sealed juncture to minimize interference with blood flow and prevent occurrence of gaps or dead space. It should be noted that the gap illustrated in FIG. 2 between edges 34 and 35 is merely for illustration of the separate structural edge for each connecting member. In reality, these two edges form a single line which would constitute the medial sealed juncture and would have no gap present. Hereafter, such sealed junctures formed in accordance with the present invention will be shown as a single line to conform to the sealed description. See, for example, FIGS. 3, 4 and 5 with their attendant descriptions.

Figure 1:
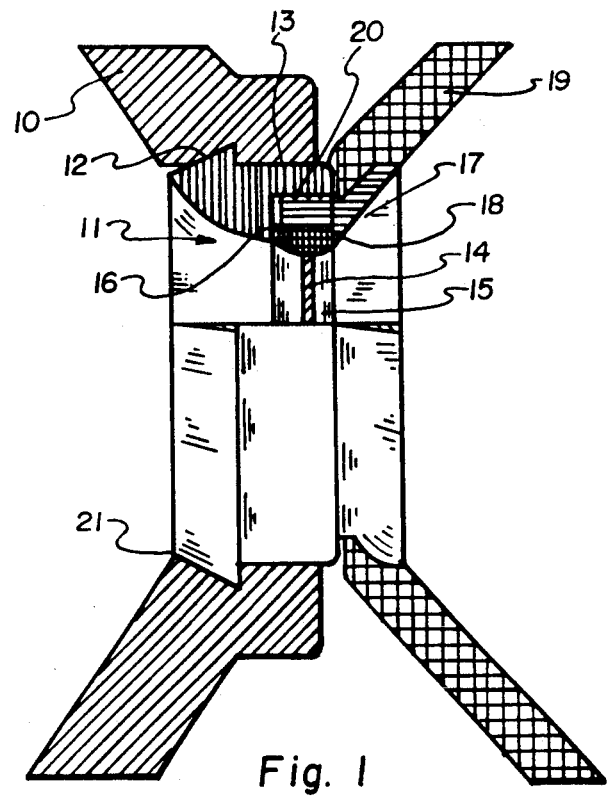
FIG. 1 shows a prior art representation of a quick-connect valve in partial cutaway view.

Whereas prior art techniques for dealing with thrombogenesis have focused on utilizing drugs such as heparin or other anti-coagulation chemicals or by treating surfaces with anti-coagulation preparations, the present invention has adopted a contrasting approach Instead, the present invention focuses on selection of materials and fabrication techniques which develop enhanced sealing contact. Instead of utilizing a soft polymer disposed in quick-connect configuration around the rigid valve holder, the present invention joins one of the open ends 24 to the other open end 25 by coupling two rigid connective members 28 and 29. Significant improvement develops because of the abandonment of the prior art technique wherein pliable material 10 (FIG. 1) on one side is coupled to a rigid connector 11 on the other side. Such prior art technique is believed to have created difficulty because of the imbalance in modulus between the respective soft and rigid members. Such use of soft-to-rigid attachment structure resulted in deformation of the soft material, forming the fatal gaps and openings which lead to thrombogenesis.

In contrast, the present invention has adopted a new and different approach to interconnecting open ends of the circulatory system. Each end is now coupled via graft material 27 to a rigid connective member 28 or 29. This enables more effective techniques of joining both members to form a totally controlled fluid path which is more independent of stresses applied at the situs of implantation.

For example, with the respective rigid connective members, each of the mating faces at the internal sealing edges 34 and 35 can be machined or otherwise prepared to a surface having much greatly improved sealing contact. In the preferred embodiment, a rigid polycarbonate composition is utilized as material for the connective members. The interior surfaces and the respective sealing faces can be machined to a very high tolerance. Other techniques exist for injection molding within the tolerance limitations to establish the required sealing contact at the medial sealed juncture. In prior art techniques where soft material was quick coupled to rigid valve housing material, such fine tolerances had little significance. For example, it was generally believed that the soft plastic quick coupled material would conform to the exterior surface of the rigid valve holder.

The desired sealing contact of mating faces at 34 and 35 is realized in the present invention by imposing a connective force 37 with respect to the first and second connective members. This force is applied substantially along the flow line 26 which is parallel with the central axis 38 (shown as colinear with the flow line 26). As shown in FIG. 2, this force 37 is applied in opposing relationship along each respective connective member and toward the internal sealing edges to establish the medial seal juncture.

These forces are developed by use of a connecting sleeve 40 which extends around the respective first and second connective members 28 and 29 and operates to pull these members toward each other in sealing contact. This connecting sleeve 40 is coupled at one side to the first connective member 28 by means of retaining flanges 41 and 42. Retaining flange 41 is formed as part of the sleeve 40 and projects radially inward at a distal edge 43 thereof. The second retaining flange 42 projects outward from the first connective member and is located more closely to the internal sealing edge 34 is an engaging configuration with respect to retaining flange 41. Accordingly, the sleeve 40 is secured in place at the first connective member 28 between the graft 27 and retaining flange 42.

In FIG. 2, the illustrated sleeve 40 is constructed of rigid material which includes inner threads 44 at an interior surface of the sleeve which extends axially beyond the internal sealing edge 34 of the first connective member. This enables engagement of the threaded portion 44 with a corresponding threaded exterior surface 45 of the second connective member. The required connective forces are applied as the threaded surface 44 engages the corresponding threaded surface 45, with appropriate rotation of the sleeve being effected to pull the respective first and second connective members into forceful contact at the medial sealed juncture.

In addition to applying the connective forces 37, the sleeve configuration enables rotational movement so that a surgeon may shift positions between the first collective member and the sleeve, even when the second connective member is loosely coupled via threads 40 and 45. This occurs because flange 41 is rotational with respect to the first connective member 28, until the opposing forces 37 bring the flange 41 in contact with opposing flange 42. Therefore, a surgeon may loosely couple the first and second connective members and then rotate the respective open ends 24 and 25 until proper positioning occurs. At that stage, the physician is free to finally rotate sleeve 40 to full contact and seated position. In addition to enabling improved rotation and placement of the respective connected parts, the present invention facilitates proper alignment of the interconnecting members. This is in contrast to the earlier quick-connect structure in which the physician had to "feel" the proper seating configuration. In fact, the physician could rarely be certain that proper alignment and sealing contact had developed, except by observing the consequences. With the present invention, the rigid first and second connective members are properly aligned and brought together in a controlled manner by use of the rotating sleeve 40.

In summary, therefore, the sleeve 40 is coupled to one of the two connective members 28 or 29 and provides means for aligning, locking and developing the connective force which properly positions the internal sealing edges and mating faces in appropriate sealing contact. In the preferred embodiment, this sleeve should be rotational with respect to its attached connective member so that appropriate positioning of the respective first and second connective members can be accomplished immediately prior to final sealing forces. The threaded configuration shown in FIG. 2 provides one mechanism for meeting these criteria. With respect to specific thread design, a quadra-lead thread design is preferred so that rotation of the sleeve through 90 degrees completes the locking procedure. Such limited rotation provides convenience to the implacing physician, as well as meeting the design criteria previously set forth.

Figure 3:
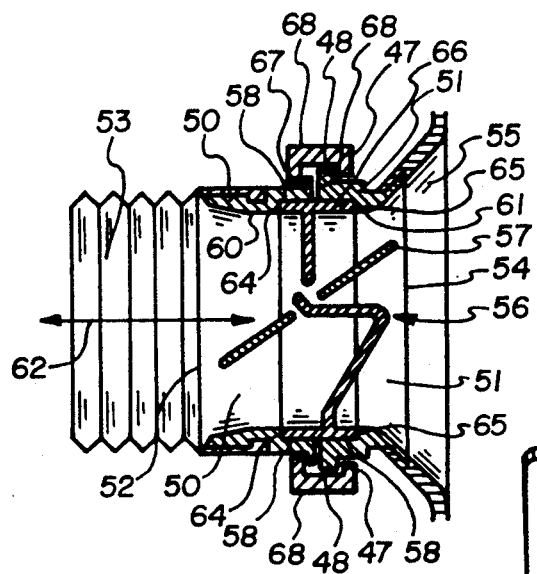
FIG. 3 shows a cross section of the present invention including a valve insert for controlling direction of blood flow.

It will be apparent to those skilled in the art that a snap-lock configuration may also be applied in place of the threaded sleeve. In this case, the sleeve comprises a ring member with a radial flange which projects inward, similar to flange 41 of FIG. 2. Likewise, a retaining flange 42 is provided in the first connective member. Instead of utilizing threads, however, the snap-on configuration (shown in FIG. 3) includes a second sleeve flange at the remaining edge 47 which engages an outward projecting flange 48 positioned on the second connective member and displaced away from the first connective member a sufficient distance to develop the required connective force pursuant to tension within the sleeve as it is extended to its engaged position at opposite sides of the projecting flanges on the first and second connective members as shown in FIG. 3.

It will be apparent to those skilled in the art that the general description provided with respect to FIG. 2 will require modification where the device is applied to specific applications. For example, the graft material 27 may be applied as a vascular graft or an atrial cuff. Other applications will require appropriate modifications in material composition and configuration. The mating faces at numerals 34 and 35 may be planer in configuration and oriented at right angles to the central axis 38 (as illustrated in FIG. 2) or may be configured with other geometries.

The important factor is that the geometry selected by adapted to form a complete seal between the mating faces. Finally, the illustrated circular configuration for the annular cross section of the device 23 has been selected because of its preferred flow dynamics. There may be circumstances where variations in this cross section would be preferred. Those skilled in the art will readily determine such modifications.

It should also be noted that the extended threaded interior surface 44 of the sleeve 40 operates as a self-alignment device. Other forms of alignment device may likewise be applied and will typically involve a structure which includes an annular flange which projects axially with respect to the device and extends from one of the connective members. The other connective member may be structured with an alignment guide (the exterior threaded surface 45 of the second connective member 29). The alignment guide is configured to receive the alignment flange as the members are connected in interlocking relationship. This provides an alignment function between the flange and guide to insure movement of the respective connective members along a common axis for proper seating and sealing in response to the connective forces 37. Other variations will be apparent from additional embodiments set forth hereafter.

Figure 6:
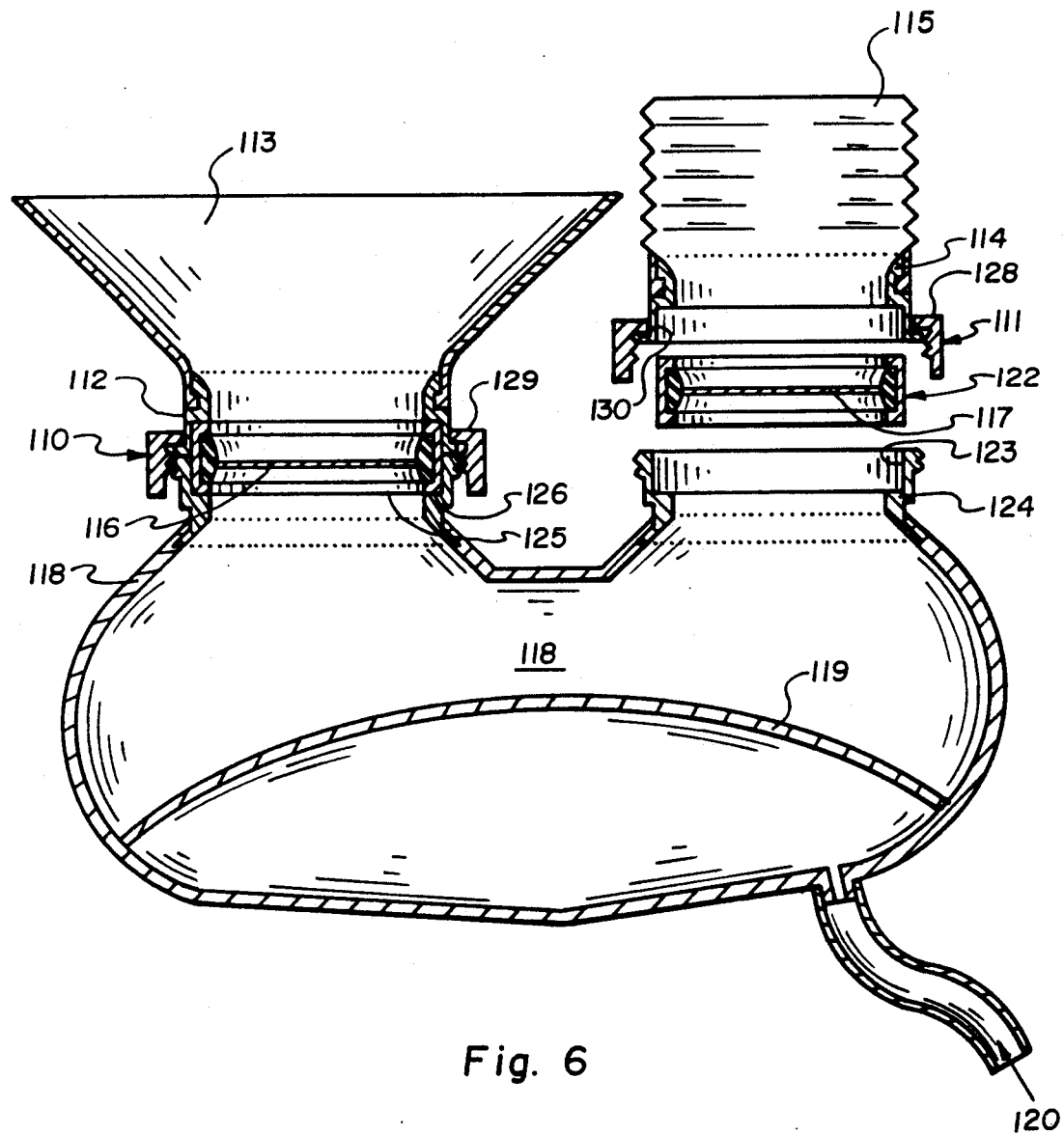
FIG. 6 portrays the placement of the present invention as shown in FIG. 5 with valves in a conventional artificial heart component.

FIG. 3 illustrates the application of the present invention to a valved tubular interconnect device. The device includes a rigid first connective member 50 and a rigid second connective member 51. The first connective member 50 includes a distal edge 52 which is coupled as previously described to a vascular graft 53. Second connective member 51 includes a distal edge 54 which is attached to a portion of the artificial heart housing 55. Such housing is typically constructed of BIOMER. An example of such a housing is shown in FIG. 6. For clarification, item 55 corresponds to item 118 in FIG. 6. A valve member 56 is coupled within at least one of the connective members to provide the desired directional control to blood flow. The valve member includes a unidirectional valve element 57 which blocks flow in one direction and passes flow in the opposite direction, and an annular support frame 58 which is recessed within the interior surfaces 60 and 61 of the connective members to avoid obstruction of the flow line 62.

The embodiment of FIG. 3 illustrates a recessed channel for the annular support frame 58 which is formed by alignment of two open-sided channels 64 and 65 which are formed at the internal sealing edge of each respective connective member 50 and 51. These open-sided channels extend axially along the interior surface 60 and 61 at a common depth to form a cross-sectional channel configuration which includes a base surface 66 and respective side walls which have been numbered as 64 and 65 (also representing the open-sided channel structure previously referenced). The internal sealing edges have been identified as 67 and 68 at the top of FIG. 3 and extend down to the interior surfaces 60 and 61 to include the base and side walls of the channel.

This channel houses a cylindrically shaped valve support frame 58. The valve support frame has exterior and interior surfaces and opposing edges which define the axial bounds of the cylinder. As has been previously indicated, the depth of the channel within the first and second connective members is equal to the cylindrical wall thickness to provide matching surface alignment of the interior cylindrical surface and the interior surfaces of the respective first and second connective members. The axial channel length is exactly equal to the cylindrical axial length of the valve support frame. The exterior surface of the cylinder and the opposing edges are formed as mating surfaces to develop sealing contact with the channel base and channel side walls respectively. Sealing contact is developed as the sleeve 68 is positioned in tension to draw the respective first and second connective members together. Sealing contact is maximized where cylinder edges are machined to a flat face perpendicular in orientation to the central axis of the cylinder and with the side channel walls likewise having a flat mating face in perpendicular orientation with the same axis.

This configuration permits the first connective member 50 to be sutured at the graft 53 to the aorta or pulmonary artery. The second connective member 51 has the valve support frame 58 adhesively fixed within the open-sided channel of the second connective member, which is already coupled to the artificial heart structure 55. Final connection of the subject invention is made when the heart 55 is placed in proper position and orientation within the patient and the respective first and second connective members are brought in position for insertion. The physician then slides the projecting portion of the valve support frame into the open-sided channel of the first connective member and makes final rotational adjustment for proper alignment of both components. Sleeve 68 is then extended and snapped across the corresponding flanges for final attachment.

Figure 4:
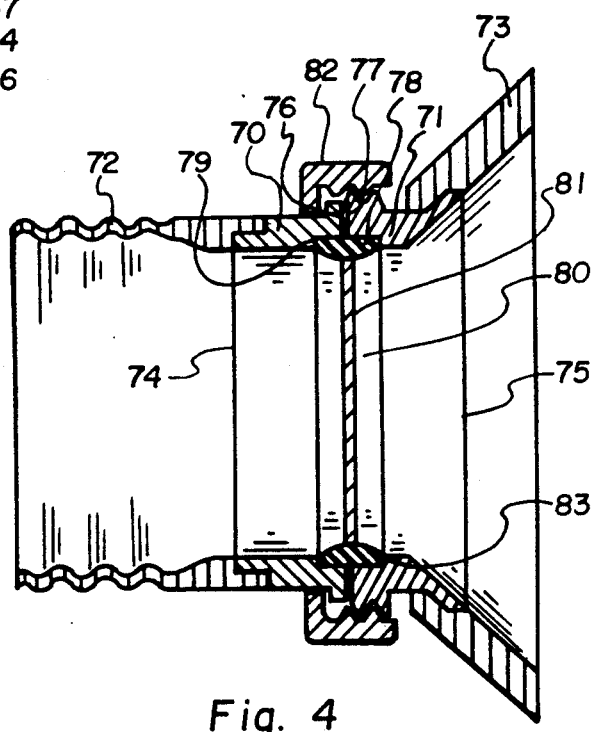
FIG. 4 shows a similar embodiment to FIG. 3 utilizing an alternate valve configuration within the invention.

FIG. 4 illustrates a similar valve support frame positioned within an interconnect device constructed in accordance with the present invention. The device includes first 70 and second 71 connective members which are respectively coupled to graft material 72 and the BIOMER of the artificial heart structure. These attachments are at the respective distal edges 74 and 75 of the first and second connective members. The internal sealing edges 76 and 77 extend down through base 78 and side wall 79 channel structure similar in design to that set forth with respect to FIG. 3, items 64, 65 and 66.

A MEDTRONICS-HALL ™ (an artificial valve assigned to Medtronic, Inc.) grooveless valve 80 is shown inserted within the recess channel and includes the valve element 81 for passing or blocking blood flow. Side walls 83 have been lengthened and prepared with parallel, flat surfaces to provide sealing contact with channel side walls. The first and second connective members 70 and 71 are constructed of ISOPLAST rigid plastic and machined in accordance with previous discussion. The valve 80 is positioned within one of the open-sided channels and is adhesively sealed in proper orientation. A sleeve member 82 having threaded configuration is positioned on the first connective element, which is then attached to the circulatory system via graft 72. Implacement of this device as part of an artificial heart implantation is done in accordance with the principles previously set forth.

Figure 5:
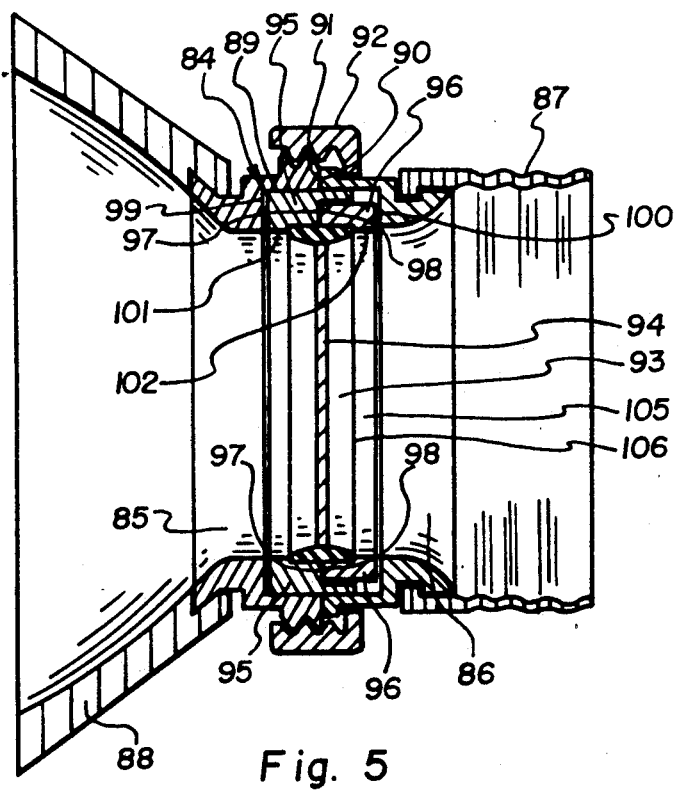
FIG. 5 shows still another embodiment of the present invention utilizing a valve insert having a separate support structure.

FIG. 5 discloses an alternate embodiment wherein the valve is positioned within a rigid annular valve attachment member 84 to form a unibody valve insert. Here again, the interconnect device comprises the first 85 and second 86 connective members. In this case, the second connective member is coupled to the graft 87 whereas the first connective member is attached to the artificial heart structure 88. In this sense, the first and second connective members will perform exact opposite functions as those set forth in the previous figures. The structure of the first and second connective members is the same as that described in FIGS. 3 and 4, including the existence of the recessed channel 89 for placement of the valve. Accordingly, recessitation of earlier discussion regarding the function of the internal sealing edges 90 and 91 will not be provided. These are brought in sealing contact by the sleeve 92 as was described in previous examples.

The valve support frame 93 and coupled valve element 94 are positioned within the annular valve attachment member 84 by first and second seating members 95 and 96. The first and second seating members are similar in design and operation to the first and second connective members previously described. Each seating member has a medial sealing edge 97 and 98. Distal edges 99 and 100 are also formed for sealing contact with the side walls of the recessed channel in the connective members. Each seating member has an interior surface 101 and 102 which extends axially inward from the distal edge and is formed to provide a biocompatible surface with respect to blood flow.

Each of the seating members includes an open-sided channel which is formed at the medial sealing edge and extends axially along the interior surface at a common depth to provide a recessed channel for receiving and retaining the valve support frame. This valve support frame is captured within the recessed channel as the seating members are brought together in common axial alignment. The valve frame is adhesively secured together with the adhesive attachment of the medial sealing edges to form the single valve insert.

This valve insert is placed within the channel formed in the first and second connective members. At least one of the seating members includes an exterior face which is formed for mating contact with the base 89 of the channel when the respective connective members are aligned and locked together.

The first and second seating members are adhesively attached at the medial sealing edges 97 and 98 with the valve support frame adhesively seated within the support frame channel. These three elements thereby become a single integral structure which can then be removably inserted within the recess channel of the first and second connective members. The primary value of this insert arises from the use of rigid plastics which can then be machined and otherwise configured to the exact dimensions of the channel formed within the rigid, plastic connective members.

Where the valve support frame comprises an annular ring having an interior surface of arcuate cross section as shown in FIG. 5, the recess channel of the seating members may include a lip at each side wall to capture the arcuate edge of the support frame more rigidly within the channel structure. This provides a more secure structure than just adhesive attachment of the ring. It also avoids any possible gaps or dead space where the metal support frame meets the seating members. The exposed interior surface 105 and juncture 106 are covered with BIOMER to further seal and protect against thrombogenesis. By utilizing the same medical grade, high durometer polyether polyurethane as is used for the connective members, temperature response and effects of the environment develop uniform changes which do not adversely affect operation of the device. In addition, exposure to the fluid environment of the circulatory system develops some expansion of the polyether polyurethane material, enhancing the sealing effect desired.

The advantages of the use of a rigid annular valve attachment member with the valve support frame as shown in FIG. 5 become apparent in review of FIG. 6. This figure discloses a conventional component of a commercial artificial heart. This component includes a pair of tubular interconnect devices 110 and 111 (the later being shown in separated view). The first connective member 112 of interconnect valve 110 is coupled to an atrial cuff 113. The first connective member 114 of interconnect valve 111 is coupled a vascular graft 115. This unit will replace, in part, the natural heart by pumping blood along a single flow direction. Accordingly, valve elements 116 and 117 will have a common flow direction. Blood passes through the pumping chamber 118 in response to a movable diaphragm 119 which is powered by air pressure 120 introduced from a pumping source. Successive inflation and collapse of the diaphragm 119 operates to circulate blood along the flow direction in accordance with well known technology.

Implantation of the artificial heart device is accomplished by inserting the valve insert 122 into the open-sided channel 123 of the second connective member 124. Likewise, the second valve insert 125 is inserted within the open-sided channel 126. This structure is then ready for insertion into the heart cavity of a patient. After proper orientation of each component, the respective interconnect devices 110 and 111 are attached at their respective positions, with the sleeves 128 and 129 being rotated into the locked and sealed configuration (as illustrated by the structure for device 110).

Based on this configuration, it is clear that all sealing surfaces are of hard plastic or other rigid form of material to enable total seal in response to the connective force applied. This structure is easily adapted for the use of the surgeon, enabling rotation of components and assurance of firm seal. In addition, all exposed surfaces to the blood can be inspected prior to insertion to insure proper sealing of junctures and absence of other adverse conditions.

The subject invention has been evaluated during the implantation of the Utah-100 pneumatic total artificial heart into 12 calves and 5 sheep. The Utah-100 artificial heart is an elliptically shaped device which operates in a manner similar to that set forth in FIG. 6. Three different connector systems were studied as part of 68 evaluations in 17 implants.

The first group of implants was made with respect to three animals and utilized a connector system (referred to in Table I as QC for quick-connect) comprised of (i) a machined, rigid polycarbonate valve-holding ring which was attached to the ventricular housing and (ii) a flexible solution-cast polymer connector which was attached to the atrial cuffs or vascular grafts. The two parts were designed to be snapped together for assembly at the time of surgery. The polycarbonate valve-holding ring was designed with two separate parts which screw together to form a pressure seal around a titanium valve ring and to secure the valve to the ventricular housing. This is the prior art structure represented in FIG. 1 previously discussed.

A second group of implants with four animals received a quick-connector which was modified by using ISOPLAST 101 TM as the material for the valve-holding ring, replacing the former polycarbonate composition (referred to in Table I as QC-M). The Isoplast permitted the use of a solvent, dimethylacetamide, to soften the Isoplast prior to assembly and to allow the polymer to mold to the contour of the titanium valve ring. This significantly reduced or eliminated the gaps in the junction between the Isoplast and the valve.

Finally, the third group of implants with ten animals received a connector system in accordance with the present invention. The connector system (referred to in Table I as CS-I) conformed generally to the structure of FIG. 5, with the first and second connective members being machined to a very high tolerance of ±0.001 inches at the side walls of the recessed channel. One of the connective members was bonded to the housing of the artificial heart, while the second was bonded to a solution-cast BIOMER TM collar which was attached to either the atrial cuff or vascular graft. The valve frame was positioned within the connector device as illustrated in FIG. 3. The valve insert comprising the valve support frame and rigid annular valve attachment member were machined from ISOPLAST 301 TM. The valve frame was solvent-sealed into this annular attachment member to form a separate and independent insert structure. This valve insert was then fastened into the outside screw ring (open-sided channel 130 in FIG. 6) which was fabricated from high-density polyethylene. The junctions formed with these connectors were high-tolerance pressure seals. The valve insert assemblies were then inspected microscopically at 20× before implantation to verify the absence of gaps between the titanium valve support frame and the Isoplast insert.

A second design (referred to as CS-II in Table I) similar to the structure illustrated in FIGS. 3 and 4 was utilized wherein the valve support frame replaced the valve insert of FIG. 5. This structure utilized a precision, tubular valve ring with parallel machined ends which formed sealing contact at channel side walls.

Three different types of valves were used in the various connector designs. BJORK SHILEY TM (an artificial valve assigned to the Shiley Co.), MEDTRONIC-HALL grooveless and MEDTRONIC-HALL extended-sided, grooveless (as 4). All of the valves used in the implants were measured with a micrometer. Variations in valve height range from 0.004 to 0.012 inches. The more pronounced variations in height were adjacent to the valve struts.

Surgical implantation in post operative care of the test animals followed methods recognized as accepted protocol. Animals were cared for in routine fashion for the duration of each experiment, having similar diets and husbandry. Chronic anticoagulation therapy in each implantation was varied, depending on the particular experimental protocol. Generally, this therapy consisted of administration of Coumadin, Persatine, aspirin, or no anticoagulation. For purposes of this study, animals living less than 90 days were considered short-term implants and animals living more than 90 days were considered long-term implants.

Experiments were ended or terminated for one of three reasons: elective termination established by the particular protocol; termination for reasons of illness or discomfort or sudden death of the animal. Heparin was routinely administered to all animals prior to death or before the devices were stopped, reducing the likelihood of postmortem clot formation in the devices. A complete necropsy was performed immediately following death. The animal was suspended in an upright position, the organs were dissected, removed and samples were taken for histopathology and bacterial culture. The presence of renal infarcts were recorded as well as abnormalities in other organs. Cultures of thrombus on the prosthetic valves were taken in most cases. The retrieved devices were inspected and evaluated, including evaluation for mechanical failure and thrombus formation. Visual examinations and photography were done at necropsy, while microscopic evaluation of the devices were performed within 24 hours following the necropsy. The connector and valve junctions were examined microscopically using a 20 × stereomicroscope, and the incidence and location of thrombus was noted.

Thrombi were identified by their characteristic appearance and were often vegetative in nature. They were composed of various combinations of fibrin, platelets, white blood cells and red blood cells as determined by histopathologic examination.

Data for the 68 connectors evaluated in the 17 animals with implants are summarized in Table I. The region above the horizontal broken line shows results arising with prior art devices QC. Results from the inventive structure is shown below this line. The information for comparison includes animal species, implant duration, anticoagulation therapy, type of connector and the incidence of thrombus formation at explant. Circled areas designate connectors and valve mount junctions experiencing thrombus formation. Dashed indicate no thrombogenesis. The letters N, C, P and A identify the anti-coagulant used, if any: None, Coumadin, Persantine and Aspirin.

TABLE I

Summary of experimental results

| Post-op Species | Anti survival days | CONNECTORS coagulant used | VALVE MOUNT JUNCTIONS | | | | | | | |
|---|---|---|---|---|---|---|---|---|---|---|
| | | | RI | RO | LI | LO | RI | RO | LI | LO |
| Calf | 25.0 | N | QC | QC | QC | QC | ○ | ○ | ○ | — |
| Calf | 268.0 | C | QC | QC | QC | QC | ○ | ○ | ○ | — |
| Calf | 16.0 | C | QC | QC | QC | QC | ○ | ○ | ○ | — |
| Calf | 92.9 | C | QC-M | QC-M | QC-M | QC-M | — | — | — | — |
| Calf | 109.9 | C | QC-M | QC-M | QC-M | QC-M | — | — | — | — |
| Sheep | 105.0 | C | QC-M | QC-M | QC-M | QC-M | — | — | — | — |
| Sheep | 44.5 | P | QC-M | QC-M | QC-M | QC-M | — | — | — | — |
| Calf | 45.0 | N | CS-I | CS-I | CS-I | CS-I | — | — | — | — |
| Sheep | 1.1 | N | CS-I | CS-I | CS-I | CS-I | — | — | — | — |
| Sheep | 20.1 | N | CS-I | CS-I | CS-I | CS-I | — | — | — | — |
| Calf | 17.9 | C | CS-II | CS-II | CS-I | CS-I | — | — | — | — |
| Sheep | 331.0 | A | CS-I | CS-II | CS-I | CS-II | — | — | — | — |
| Calf | 106.0 | C | CS-I | CS-II | CS-I | CS-II | — | — | — | — |
| Calf | 94.3 | C | CS-I | CS-I | CS-I | CS-I | — | — | — | — |
| Calf | 1.0 | N | CS-I | CS-I | CS-I | CS-I | — | — | — | — |
| Calf | 109.0 | C | CS-I | CS-I | CS-I | CS-I | — | — | — | — |
| Calf | 138.0+ | C | CS-I | CS-I | CS-I | CS-I | | | NA | |
| Calf | 18.0 | C | CS-I | CS-I | CS-I | CS-I | — | — | — | — |

TABLE II

Incidence of Thrombus Formation Observed at Connector Junctions at Explantation

| Connector Position | Connector Junction Type | | | | | |
|---|---|---|---|---|---|---|
| | QC | | QC-M | | CS-I (Invention) | |
| RI | 2/3 | (67%) | 0/4 | (0%) | 0/9 | (0%) |
| RO | 2/3 | (67%) | 1/4 | (25%) | 0/7 | (0%) |
| LI | 1/3 | (33%) | 2/4 | (50%) | 0/10 | (0%) |
| LO | 1/3 | (33%) | 1/4 | (25%) | 0/8 | (0%) |
| Totals | 6/12 | (50%) | 4/16 | (25%) | 0/34 | (0%) |

Table II details the data for each connector junction type by position within the artificial heart implant. References to RI and RO indicate Right Inflow and Outflow respectively. References to LI and LO represent Left Inflow and Outflow. In the quick-connector group representing the initial prior art study, 6 of 12 of the quick-connector junctions showed thrombus while 4 of 16 of the second modified quick-connector junctions showed thrombus. In the third group utilizing the present invention, none of the 34 connector junctions showed evidence of thrombus.

The incidence and location of sub- and supravalvular thrombus associated with the valve mounting junctions of the 4 types of valve mounting designs are presented in Table III.

TABLE III

Incidence of Thrombus Formation Observed at Valve Mounts at Explantation

| Valve Position | Valve-Mounting System | | | | | | | |
|---|---|---|---|---|---|---|---|---|
| | QC | | QC-M | | CS-I | | CS-II | |
| RI | 3/3 | (100%) | 0/4 | (0%) | 2/9* | (22%) | 0/1 | (0%) |
| RO | 3/3 | (100%) | 0/4 | (0%) | 0/7 | (0%) | 0/3 | (0%) |
| LI | 3/3 | (100%) | 0/4 | (0%) | 0/10 | (0%) | 0/0 | (0%) |
| LO | 1/3 | (100%) | 1/4 | (25%) | 1/8 | (13%) | 0/2 | (0%) |
| Totals | 10/12 | (83%) | 1/16 | (6%) | 3/34 | (9%) | 0/6 | (0%) |

*Includes one valve noted to be improperly mounted and another valve with a manufacturing defect Ten of the 12 (83%) in the quick-connector group 1 exhibited thrombus formation, and 1 of 16 (6%) in the QC-M group 2 showed thrombus. In the CS-I valve mounts (group 3), 3 of 34 (9%) displayed thrombus. The implants that utilized the CS-II valve mount revealed no sub- or supravalvular thrombus in the 6 valve mounts evaluated. When the groups that utilized the design in which the valve mounts were sealed (QCM, CS-I and CS-II) are combined, the total 56 valve mounts showed 4 (7%) valve mounts with thrombus.

Of the 34 valve junctions involving structures similar to FIG. 5, 32 were verified as sealed with no visible gaps. One of the valves had a large, surface irregularity or indentation adjacent to one of the struts that was beyond the limits of the mounting technique for achieving a complete seal. The result was a macroscopic gap. This valve was implanted twice and exhibited thrombus formation exclusively at this gap on both occasions. One other insert had a gap caused by the misalignment of the titanium valve ring in the Isoplast insert. Thrombus occurred at this gap. Only one of the 32 valve-mount junctions that were verified as having no visible irregularities exhibited thrombus formation.

The duration of the experiments ranged from one to 331 days, with a mean survival time of 82 days. There were eight long-term survivors and nine short-term survivors.

Microscopic examination of the quick connector prior art embodiments in the first three implants showed that all connectors where thrombus had formed, gaps or other irregularities were visible at the connector junctions. This evidenced the difficulty of manufacture for a high-tolerance quick-connector junction utilizing polyurethane materials. In all implants using the quick-connector system of the prior art, thrombus was most prominent in the area adjacent to the valve struts. Microscopic examination of these valve mounts disclosed gaps between the valve ring and polycarbonate holding ring in every instance.

In the second group of implants, the only thrombus observed in valve mount junctions was associated with a gap behind one of the valve struts which had not been adequately sealed. Connector-associated thrombus formation did not correspond to valve-associated thrombus formation.

In the third group of experiments utilizing the present invention, dramatic improvement was realized. The utility of designing interconnect systems which use rigid connective members at each side of the junction is clearly superior to the prior art methods of soft-to-hard and soft-to-soft connective junctions.

In addition to the success of reducing thrombus formation to almost zero, the present invention provides improved convenience to the surgeon during implantation. The cuff or graft connector can be more easily rotated to proper position to insure that alignment of the artificial heart is correct. Screw rings can then be tightened to maintain that proper orientation. If replacement of a valve or complete ventrical is required, the procedure is simplified. Each part can be quickly changed without resuturing. This is in contrast to required removal of much of the prior art device in order to change a single component.

It will be apparent to those skilled in the art that other variations beyond those disclosed in the examples set forth are possible. Accordingly, it is to be understood that the subject invention is to be limited only by the following claims, and not by the specific examples.

I claim:

1. A tubular interconnective device for coupling open ends of a flow line as part of a circulatory system of a living being, said device comprising:
   first and second separable rigid tubular connective members, each of said connective members having continuous interior surfaces of biocompatible material suitable for contact with blood;
   pliable attachment means connected to a distal end of at least one of said connective members,
   valve means coupled with at least one of said connective members for providing directional control of blood flow within the device,
   said first connective member having a first sealing edge at a proximal end thereof and said second connective member having a second sealing edge at a proximal end thereof, and
   means for aligning and locking said first and second sealing edges in a coaxial configuration thereby forming a smooth continuous and biocompatible interior surface extending from each end of the valve means to the interior surfaces of the respective first and second connective members.

2. A device as defined in claim 1 wherein the connection between said pliable attachment means and said distal end of said at least one connective member comprises a smooth continuous biocompatible interior surface which minimizes thrombosis and interference with blood flow.

3. A device as defined in claim 1 wherein said pliable attachment means includes means for attachment to living tissue as part of the circulatory system.

4. A device as defined in claim 1 wherein said first and second connective members are circular in annular cross-section.

5. A device as defined in claim 1 wherein the biocompatible material comprises a polyether polyurethane material coating.

6. A device as defined in claim 1 wherein the sealing edges form planar surfaces which are oriented perpendicular to a central axis defined by the aligned connective members.

7. A device as defined in claim 1 wherein said device includes means for attachment to an artificial heart implant.

8. A device as defined in claim 1 wherein at least one of said connective members includes a self-alignment, annular flange projecting axially outwardly of the connective members, the other connective member having an alignment guide configured to receive said alignment flange as the members are connected in interlocking relationship, the respective flange and guide being operable to align both connective members along a common axis for proper seating and sealing in response to connective forces.

9. A device as defined in claim 1 wherein said connective members are formed of a rigid polycarbonate composition capable of being machined to proper tolerances for sealing upon interlocking in response to connective forces.

10. A device as defined in claim 1 wherein said pliable attachment means is connected to a distal end of each of said first and second connective means.

11. A device as defined in claim 1 wherein said means for aligning and locking comprises a connecting sleeve coupled at one side to said first connective member, said second connective member and said sleeve further including means for interattachment and for imposition of connective force along each of said connective members and toward the said sealing edges to establish said medial sealed juncture.

12. A device as defined in claim 1 including thread means on the sleeve to allow rotatable and axial displacement of said sleeve respect to the attached first connective member to enable relative axial displacement and positioning of the connective members with respect to said sleeve.

13. A device as defined in claim 1 wherein said valve insert comprises a unidirectional valve element which blocks flow in one direction and displaces to pass flow in the opposite direction, said valve element being positioned within the device by an annular valve support frame which is recessed within the interior surfaces of the connective members to avoid obstruction of the flowline.

* * * * *